United States Patent [19]

Callahan

[11] 4,338,817
[45] Jul. 13, 1982

[54] HYDROMETER WITH IMPROVED TEMPERATURE COMPENSATION

[76] Inventor: George E. Callahan, Feldstrasse 34, 4000 Dusseldorf 30, Fed. Rep. of Germany

[21] Appl. No.: 145,889

[22] Filed: May 2, 1980

[51] Int. Cl.$^3$ .............................................. G01N 9/12
[52] U.S. Cl. ......................................... 73/448; 73/449
[58] Field of Search ................... 73/449, 448, 444, 451

[56] References Cited

U.S. PATENT DOCUMENTS

| | | | |
|---|---|---|---|
| 1,972,220 | 9/1934 | Edelmann | 73/448 |
| 2,067,914 | 1/1937 | Godfrey | 73/448 |
| 2,221,913 | 11/1940 | Edelmann | 73/448 |
| 2,301,273 | 11/1942 | Greene et al. | 73/449 |
| 2,853,881 | 9/1958 | Chandler | 73/449 |
| 3,055,220 | 9/1962 | Ryan et al. | 73/448 X |
| 3,538,773 | 11/1970 | Goldberg | 73/451 |
| 3,808,893 | 5/1974 | Jinno et al. | 73/449 |

*Primary Examiner*—Daniel M. Yashich
*Attorney, Agent, or Firm*—William R. Hinds

[57] ABSTRACT

For measuring the density of fluids whose densities lie within a predetermined range and whose coefficients of thermal expansion vary within this range, a stem hydrometer has a lower body volume which extends up to the lowest marking on the density scale and is immersed when the hydrometer is buoyant in a fluid at the highest part of the density range, a scale volume which extends between the lowest and highest markings on the density scale and is immersed with the body volume when the hydrometer is buoyant in a fluid at the lowest part of the density range, and a stem volume above the highest scale marking. The body volume has a coefficient of expansion substantially equal to that of the fluid at the highest part of the range, and the scale volume is comprised of material such that the coefficient of expansion of the combined body volume and scale volume is substantially equal to that of the fluid at the lowest part of the range. The total mass of the hydrometer takes into account the apparent additional mass resulting from surface tension of the fluid. For fluids whose coefficients of expansion change disproportionately with density, combinations of materials may be used in the scale volume so as to vary the coefficient of expansion along the scale volume in keeping with disproportional changes in that of the fluid.

3 Claims, 11 Drawing Figures

HYDROMETER WITH IMPROVED TEMPERATURE COMPENSATION

FIELD OF THE INVENTION

The present invention relates to devices, particularly stem hydrometers, for measuring the density of fluids. In particular, it is concerned with improving the temperature-error correction, so that accurate measurements can be made over a wide range of temperatures.

Because of thermal-expansion effects, density measurements made at different temperatures are subject to temperature error, i.e. the density reading in a fluid at temperature T is different from that made in the same fluid at a different temperature $\theta$. The present invention provides means for correcting the temperature error over a wide range of temperatures and densities, particularly when—as is often the case—the coefficient of thermal expansion of the fluid is a variable function of both temperature and density.

DESCRIPTION OF THE DRAWINGS

In order that the invention may be clearly understood and readily carried into effect, examples of fluid-density measuring devices in accordance therewith and their relationship to the prior art, insofar as that is known, will now be described with reference to the accompanying drawings, in which:

FIG. 6a shows an embodiment of the prior art in an application involving real materials;

FIG. 6b shows an embodiment of the present invention corresponding to FIG. 6a;

BACKGROUND OF THE INVENTION

Since the coefficient of thermal expansion of glass is much smaller than that of most fluids, density measurements made at different temperatures with conventional glass hydrometers are subject to large temperature errors. This has led to the proposal of hydrometers made, for instance, of molded plastics which have relatively larger coefficients of thermal expansion. Such plastic hydrometers have been proposed either with a ballast means to provide additional mass and to encourage the device to float upright, or without such ballast means, in which case the hydrometer is guided in an upright position inside a vertical tube or channel wherein the hydrometer is buoyant in the fluid. In conjunction with this, it has been proposed to make the hydrometer of a material which has substantially the same coefficient of thermal expansion as that of the fluid, so that temperature error will be minimized.

A closer examination of the thermal-expansion characteristics of most fluids reveals that these have different coefficients of thermal expansion at different densities. Therefore, complete temperature compensation (elimination of temperature error) can be achieved for only a single fluid density, i.e. at which the thermal expansion of the hydrometer is identical with that of the fluid. Other densities of the same fluid, having other coefficients of thermal expansion, would still be subject to temperature error in all measurements not made at the standard temperature for which the device was calibrated.

With regard to materials in which the coefficient of thermal expansion may vary with temperature, thermal expansion can be expressed by the dimensionless relation between a length L at the standard temperature and the change in this length $\Delta L$ at a different temperature $\theta$. Thus, at temperature $\theta$, any standard-temperature length L will be changed by the factor $$1 + \frac{\Delta L}{L},$$

and this changed length will be $$L_\theta = L\left(1 + \frac{\Delta L}{L}\right).$$

Since $\Delta L$ is small, the resulting change in volume can be taken to be $3\Delta L$, so that the standard-temperature volume V will be changed to $$V_\theta = V\left(1 + 3\frac{\Delta L}{L}\right).$$

This volume change obviously results in an inverse density change, so that $$\rho_\theta = \frac{\rho}{1 + 3\frac{\Delta L}{L}}.$$

Figure 1:
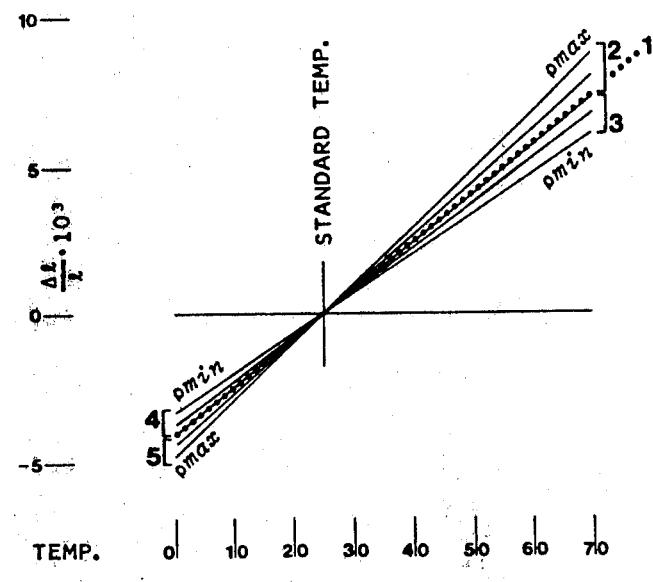
FIG. 1 shows idealized thermal expansion curves typical of those encountered in practice.

For a more ready understanding of thermal effects in devices of the present type, the thermal expansion typical of the materials in question can, for the sake of simplicity, be assumed to be a linear function of temperature change. Under this assumption, the thermal expansion curves of a typical fluid would appear as straight lines as shown in FIG. 1, where the fluid density is assumed to vary from a minimum density $\rho_{min}$ with a coefficient of thermal expansion $$\frac{\Delta L}{L} (\rho_{min})$$

to a maximum density $\rho_{max}$ with a coefficient of thermal expansion $$\frac{\Delta L}{L} (\rho_{max}).$$

The thermal expansion curves of the intermediate fluid densities lie between these extremes. Curve 1 would then represent the thermal expansion of the hydrometer material which best "averages" the thermal expansion of the fluid within the given density range, thereby providing the best possible temperature compensation. From FIG. 1 it is apparent that complete temperature compensation is achieved only in the middle of the density range, and that at extreme temperatures and densities, indicated by 2, 3, 4 and 5, temperature error is unavoidable. This temperature error obviously results from discrepancies between the thermal expansion of the fluid and that of the hydrometer at any given temperature and density, and its magnitude is such that the reliability of the device can be significantly impaired.

DESCRIPTION OF THE PREFERRED EMBODIMENTS

Figure 2:
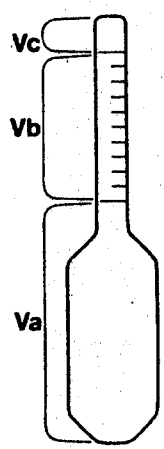
FIG. 2 shows a stem hydrometer divided into parts significant to the present invention.

The present invention provides means for correcting this temperature error, as can be understood with reference to FIG. 2. In FIG. 2, the total volume of the hydrometer is divided into three significant volumes, here designated as the body volume $V_a$, which is the volume of the body of the hydrometer up to the lowest marking of the hydrometer scale; the scale volume $V_b$, which is the volume between the lowest and the highest marking of the hydrometer scale; and the stem volume $V_c$, which is the remaining volume above the highest marking of the hydrometer scale. When the hydrometer is buoyant in a fluid at the highest part of the density range, only volume $V_a$ is immersed in the fluid. When the hydrometer is buoyant at the lowest part of the density range, both volumes $V_a$ and $V_b$ are immersed in the fluid. Volume $V_c$ is necessary in order to permit accurate readings at the lowest fluid density, and, as will be explained later, the size of this volume can serve to regulate the mass of the hydrometer, so that volumes $V_a$ and $V_b$ can be accurately predetermined.

According to the invention, volume $V_a$ is comprised of a material or combination of materials such that the coefficient of thermal expansion of volume $V_a$ is substantially the same as that of the fluid at the highest part of the density range. At the same time, volume $V_b$ is comprised of a material or combination of materials such that the coefficient of thermal expansion of the combined volumes $V_a$ and $V_b$ is substantially the same as that of the fluid at the lowest part of the density range. In terms of the previously stated expressions for the density and thermal expansion of the fluid, and writing the thermal expansion of volume $V_a$ simply as $$\frac{\Delta a}{a}$$

and that of volume $V_b$ simply as $$\frac{\Delta b}{b},$$

the above conditions are fulfiled when $$\frac{\Delta a}{a} \simeq \frac{\Delta L}{L} (\rho_{max}) \text{ and } \frac{V_a \frac{\Delta a}{a} + V_b \frac{\Delta b}{b}}{V_a + V_b} \simeq \frac{\Delta L}{L} (\rho_{min}) \quad (1),(2)$$

Figure 3:
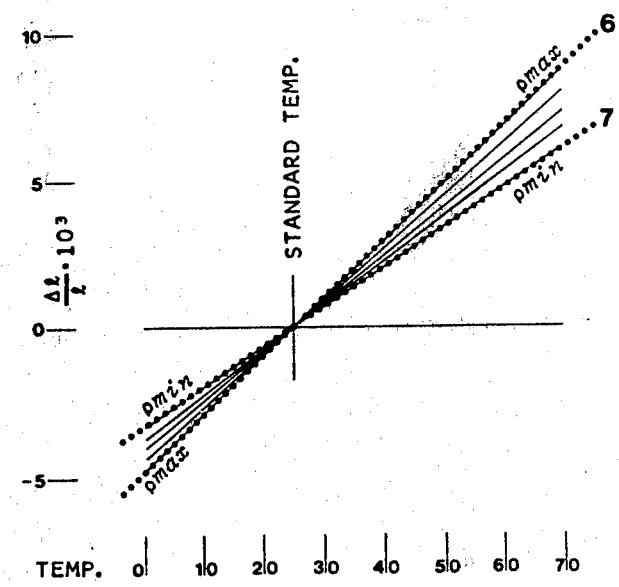
FIG. 3 is analogous to FIG. 1, but illustrative of the concept of the present invention.

FIG. 3 shows the resulting thermal expansion curve 6 for volume $V_a$ and curve 7 for the combination of volumes $V_a$ and $V_b$ in relation to the thermal expansion curves of the fluid as shown in FIG. 1. Because of the coincidence of the curves at both the highest and lowest densities, temperature error is avoided. At densities intermediate between these extremes, the thermal expansion of the hydrometer is governed by the relation between volume $V_a$ and the immersed portion of volume $V_b$, and is therefore proportional to the density of the fluid. Since the same proportionality applies substantially to the thermal expansion of the fluid at intermediate densities, the thermal expansion of the hydrometer is at all times analogous to that of the fluid, so that temperature error is avoided through the entire measuring range of the instrument.

Figure 4A:
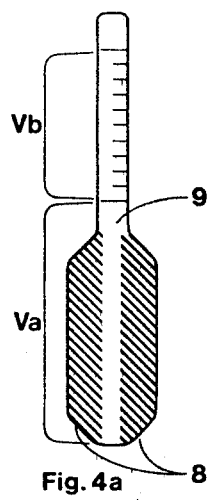
FIGS. 4a and 4b show an embodiment of the present invention.
Figure 4B:
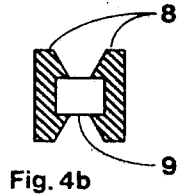

FIGS. 4a and 4b show an example of an embodiment of the invention in the form of a molded plastic hydrometer which is composed of two different materials. Volume $V_b$ consists of a material 9, whereas volume $V_a$ is formed by a structural combination of material 9 with a material 8. Since a circular cross-section is in no way mandatory to the functioning of hydrometers, the cross-section of volume $V_a$ might be arranged as shown in FIG. 4b, in order that both materials may assume the temperature of the fluid in which the hydrometer is immersed within a short time.

Figure 5:
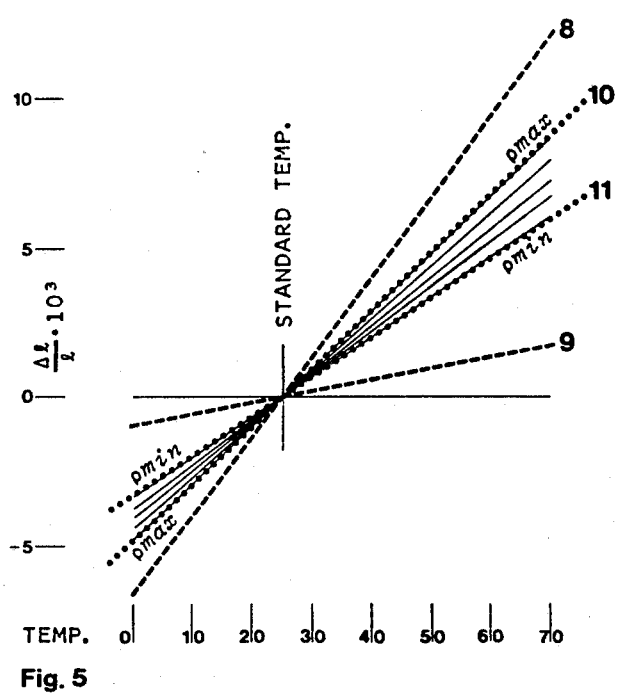
FIG. 5 shows thermal-expansion curves corresponding to the embodiment of FIGS. 4a and 4b.

In order to achieve full temperature compensation in a fluid as previously characterized, the thermal expansion of material 8 should be greater than that of the fluid at highest density, whereas the thermal expansion of material 9 should be less than that of the fluid at lowest density. This assumption is shown graphically in FIG. 5, where curve 8 indicates the thermal expansion of material 8, and curve 9 that of material 9. At the highest fluid density, volume $V_a$ is immersed, and it may be composed of 65% material 8 and 35% material 9. The thermal expansion of volume $V_a$ would therefore lie proportionally between those of materials 8 and 9, as shown by curve 10. At the lowest density, both volumes $V_a$ and $V_b$ would be immersed, and since $V_b$ consists solely of material 9, the relative proportion would be 40% material 8 and 60% material 9. Here again, the immersed volume would have a thermal expansion reflecting this proportion, as shown by curve 11. Obviously, similar results would be obtained by using other materials with other coefficients of thermal expansion in different proportions.

It was stated that the linearized thermal-expansion curves used to illustrate the foregoing examples are idealized depictions of the properties of real materials. The conclusions drawn from the examples are, however, quite independent of the linearity of thermal expansion. In practice, it will be found that the thermal-expansion curves of a wide range of suitable hydrometer materials are similar in character to the thermal-expansion curves of most aqueous solutions. In both cases, the curves show an increase in the coefficients of thermal expansion with increasing temperature, and because of this similarity, numerous suitable materials can be combined in accordance with the foregoing principles for use with different fluids.

In practical applications of the present invention, it is obvious that the effective size of volumes $V_a$ and $V_b$ will depend upon the actual depth of immersion of the hydrometer. Since immersion is governed by the mass of the hydrometer, this must be accurately predetermined. Offhand, it might be said that hydrometer mass M could be taken from a simple buoyancy calculation, for example $M = V_a \rho_{max} = (V_a + V_b) \rho_{min}$, but in practice it will be found that surface tension acting upon the buoyant hydrometer will cause an increase of immersion depth which would significantly alter the required volumetric relations. For this reason, it is within the scope of the present invention to provide means for accurately compensating for surface-tension effects, so that the hydrometer will float at a predetermined depth of immersion.

If the surface tension of the fluid is $\sigma$ (dyn/cm), the resulting increase in depth of immersion $\Delta d$ can be taken as a good approximation from $$\Delta d \simeq \frac{\sigma C}{981 A \rho},$$

where C is the circumference and A the area of the hydrometer cross-section at the level of the fluid surface. Since $\Delta d$ is a function of fluid density, it is at present more convenient to assume the increased immersion to result from an apparent additional mass $$\Delta m \simeq \frac{\sigma C}{981},$$

which is independent of the variable density term. This may be thought of as being the mass of fluid which is raised above the free surface by capillary attraction to the hydrometer. For the purpose of buoyancy calculations, the total mass of the hydrometer would then be defined as $$M = M_a + M_b + M_c + \frac{\sigma C}{981},$$

where $M_a$, $M_b$, and $M_c$ are the mass of volume $V_a$, $V_b$, and $V_c$, respectively. In order that the advantages of the present invention may be fully realized in practice, the hydrometer also comprises a stem volume $V_c$ of density $\rho_c$, which is so dimensioned that $$V_c = \left( V_a \rho_{max} - M_a - M_b - \frac{\sigma C}{981} \right) \frac{1}{\rho_c} \quad (3)$$

It has been said that hydrometers may be either ballasted or unballasted. In the case of the former, the density of ther materials is not often critical, since the total mass of the hydrometer can be controlled by varying the mass of the ballast. In the case of the latter, th? total mass would be controlled by dimensioning volume $V_c$ in agreement with equation (3). The extent of this means is, however, limited by the fact that the unballasted hydrometer would be excessively "top-heavy", and therefore subject to increased friction within the guiding tube in which it is buoyant, if volume $V_c$ were to be excessively enlarged. (A certain minimum volume $V_c$ is of course necessary in order to prevent inadvertent total immersion of the hydrometer in the lower part of the density range). In this case, the density of hydrometer materials would be critical, and it remains to be demonstrated that the foregoing principles can be put into practice under stringent conditions where real materials must simultaneously satisfy both density and thermal-expansion requirements in applications with real fluids.

Figures 6A, 6B:
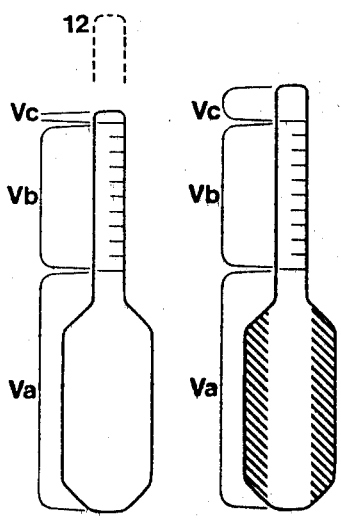

The most common example would be density measurements involving sulphuric-acid solutions, where the corrosiveness of the fluid practically precludes the use of metallic ballast. Measurements made with glass hydrometers are subject to large temperature errors, but unballasted hydrometers of molded polystyrene can be used, since this material has an appropriate density, a larger coefficient of thermal expansion, and sufficient chemical resistance. The most frequently used density range is from 1100 kg/m$^3$ to 1300 kg/m$^3$, and FIG. 6a shows to scale an appropriate polystyrene hydrometer of density 1050 kg/m$^3$. It will be noted that the stem volume $V_c$ is barely sufficient to ensure functioning of the hydrometer at the lowest fluid density, but less dense materials (e.g. polyethylenes) would require a much larger volume $V_c$, as shown by contour 12, and would therefore be unacceptable. Thus, FIG. 6a represents an optimal hydrometer for this case according to the prior art.

FIG. 6b shows to the same scale an embodiment of the present invention for this case, and having volumes $V_a$ and $V_b$ identical with those of the hydrometer in FIG. 6a. Volumes $V_b$ and $V_c$ consist of SAN (styrene acrylonitrile) copolymer of density 1080 kg/m$^3$, whereas volume $V_a$ is a combination of 53% SAN and 47% polyethylene of density 917 kg/m$^3$. Here it will be seen that the resulting volume $V_c$ is well-proportioned, and that therefore this combination of materials satisfies the density requirements fully.

Figure 7:
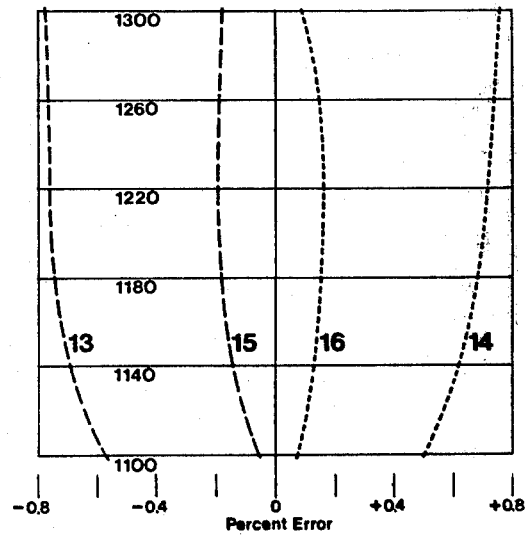
FIG. 7 shows the actual temperature error of the embodiments of FIGS. 6a and 6b.

FIG. 7 shows the temperature error of each of these hydrometers as a percent of indicated density when the fluid temperature is assumed to vary from 10° to 60° C. Although the temperature error of the hydrometer of FIG. 6a is less than that of a glass hydrometer, it will be seen to vary from a maximum of about −0.8% at 10° C. (curve 13) to +0.8% at 60° C. (curve 14). The corresponding curves 15 and 16, which apply to the hydrometer of FIG. 6b, show a temperature error nowhere greater than ±0.2%, i.e. an improvement in temperature compensation by a factor of 4.

Figure 8:
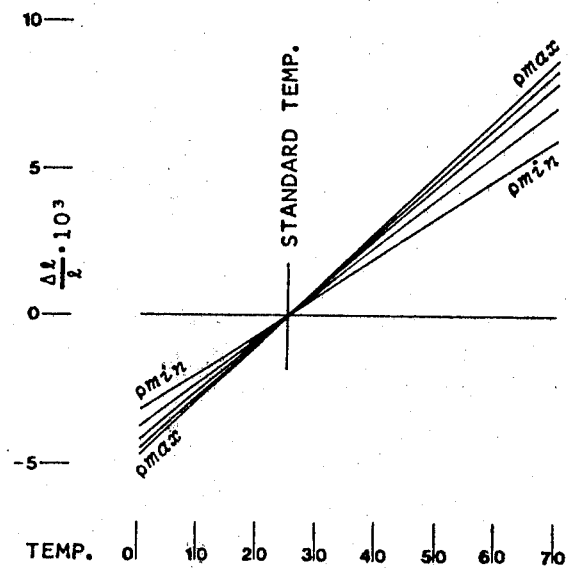
FIG. 8 is analogous to FIGS. 1 and 3, but applicable to a different fluid.
Figure 9:
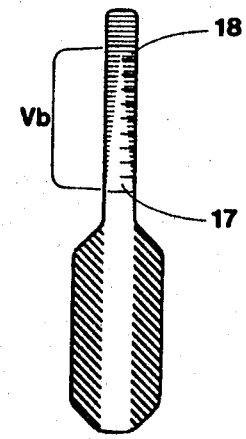
FIG. 9 shows another embodiment of the present invention appropriate to the fluid of FIG. 8.

In the foregoing example, FIG. 6b represents the simplest possible embodiment of the invention, i.e. an unballasted hydrometer consisting of only two materials. In cases where temperature compensation would be subject to very stringent requirements, it would of course be within the scope of the present invention to combine more than two materials in such a way that the thermal expansion of the hydrometer would be in even closer agreement with that of the fluid. As an example, FIG. 8 shows thermal-expansion curves of a fluid where the change in coefficients of thermal expansion is disproportional to the change in density, i.e. where thermal expansion decreases more rapidly with decreasing density. For this case, a preferred embodiment of the invention could be that shown in FIG. 9, where volume $V_b$ comprises a combination of a material 17 with a material 18. In order for the thermal expansion of the hydrometer to be analogous with that of the fluid as characterized in FIG. 8, the thermal expansion of material 18 would be less than that of material 17, whereby the thermal expansion of the immersed volume of the hydrometer would also decrease more rapidly with decreasing density.

It will be understood that the constant 981 used herein designates the acceleration of gravity (g) in the centimeter-gram-second system, and is dimensionally compatible with surface tension in dyn/cm. When using other systems, appropriate different gravity acceleration constants should be used.

I claim:

1. A hydrometer for measuring the density of a fluid having a density within a predetermined range and a coefficient of thermal expansion that varies within this range, comprising a lower body volume $V_a$ which is equal to the total mass of the hydrometer divided by the density of said fluid at the highest part of said range, and an intermediate scale volume $V_b$ which together with said volume $V_a$ is equal to the total mass of the hydrometer divided by the density of said fluid at the lowest part of said range, and an upper stem volume $V_c$, whereby said volume $V_a$ is comprised of one or more materials so proportioned that the coefficient of thermal expansion of said volume $V_a$ is approximately equal to that of the fluid at the highest part of said range, and said volume $V_b$ is comprised of one or more materials so proportioned that the coefficient of thermal expansion of the combined said volumes $V_a$ and $V_b$ is approximately equal to that of said fluid at the lowest part of said range.

2. A hydrometer according to claim 1, wherein the mass of said stem volume $V_c$, when added to the combined masses of said volumes $V_a$ and $V_b$, is equal to the product of said volume $V_a$ and the density of said fluid at the highest part of said range, less the apparent additional mass resulting from the surface tension of said fluid, said apparent additional mass being calculated as the product of the surface tension of the fluid and the circumference of the hydrometer at the level of the fluid surface, divided by the acceleration of gravity.

3. A hydrometer according to claim 1 for use with fluids whose coefficients of thermal expansion change disproportionally with density, wherein said scale volume $V_b$ is comprised of at least two materials which have different coefficients of thermal expansion and which are unequally distributed within said volume $V_b$, so that the lower part of said volume $V_b$ has a coefficient of thermal expansion different from that of the higher part of said volume $V_b$.

* * * * *